United States Patent
Glukhovsky et al.

(10) Patent No.: US 7,561,908 B2
(45) Date of Patent: *Jul. 14, 2009

(54) SYSTEM AND METHOD FOR CHANGING TRANSMISSION FROM AN IN VIVO SENSING DEVICE

(75) Inventors: Arkady Glukhovsky, Nesher (IL); Baruch Erlich, Qiryat Tivon (IL)

(73) Assignee: Given Imaging Ltd., Yoqnearn (IL)

( * ) Notice: Subject to any disclaimer, the term of this patent is extended or adjusted under 35 U.S.C. 154(b) by 8 days.

This patent is subject to a terminal disclaimer.

(21) Appl. No.: 11/140,291

(22) Filed: May 31, 2005

(65) Prior Publication Data

US 2005/0222490 A1    Oct. 6, 2005

Related U.S. Application Data

(63) Continuation of application No. 10/200,548, filed on Jul. 23, 2002, now Pat. No. 6,934,573.

(60) Provisional application No. 60/306,872, filed on Jul. 23, 2001.

(51) Int. Cl.
*A61B 5/05* (2006.01)
*A61B 6/00* (2006.01)

(52) U.S. Cl. ................. 600/407; 600/476

(58) Field of Classification Search ............ 600/407, 600/302, 476; 128/903; 348/76, 185
See application file for complete search history.

(56) References Cited

U.S. PATENT DOCUMENTS

| | | | |
|---|---|---|---|
| 3,971,362 A | 7/1976 | Pope et al. | |
| 4,278,077 A | 7/1981 | Mizumoto | |
| 4,689,621 A | 8/1987 | Kleinberg | |
| 4,844,076 A | 7/1989 | Lesho et al. | |
| 5,279,607 A | 1/1994 | Schentag et al. | |
| 5,477,858 A | 12/1995 | Norris et al. | |
| 5,604,531 A | 2/1997 | Iddan et al. | |
| 5,819,736 A | 10/1998 | Avny et al. | |
| 5,928,159 A | 7/1999 | Eggers et al. | |
| 6,018,650 A * | 1/2000 | Petsko et al. | ............. 455/234.1 |
| 6,240,312 B1 | 5/2001 | Alfano et al. | |

(Continued)

FOREIGN PATENT DOCUMENTS

DE    34 40 177    5/1986

(Continued)

OTHER PUBLICATIONS

The Radio Pill Rowlands, et al , British Communications and Electronics, Aug. 1960 pp. 598-601.

(Continued)

*Primary Examiner*—Eric F Winakur
*Assistant Examiner*—Michael T Rozanski
(74) *Attorney, Agent, or Firm*—Pearl Cohen Zedek Latzer LLP

(57) ABSTRACT

A device and system enables obtaining data such as in vivo images from within body lumens or cavities, such as images of the gastrointestinal (GI) tract. A device may include an imaging system and a radio frequency (RF) transmitter for transmitting signals from an imaging device to a receiving system. The signal strength of the transmitter may be varied or changed to account for, for example, the amount of signal attenuation resulting from body tissues.

18 Claims, 2 Drawing Sheets

U.S. PATENT DOCUMENTS

| | | | |
|---|---|---|---|
| 6,438,405 | B1 | 8/2002 | Mooney et al. |
| 6,535,243 | B1 * | 3/2003 | Tullis ..................... 348/207.1 |
| 6,546,276 | B1 | 4/2003 | Zanelli |
| 6,587,711 | B1 | 7/2003 | Alfano et al. |
| 7,061,523 | B2 * | 6/2006 | Fujita et al. ................... 348/77 |
| 7,160,258 | B2 * | 1/2007 | Imran et al. ................. 600/593 |
| 2002/0010390 | A1 * | 1/2002 | Guice et al. ................. 600/300 |

FOREIGN PATENT DOCUMENTS

| | | |
|---|---|---|
| JP | 4109927 | 4/1992 |
| JP | 5015515 | 1/1993 |
| WO | WO 01/08548 | 2/2001 |
| WO | WO 01/50941 | 7/2001 |
| WO | WO 01/65995 | 9/2001 |

OTHER PUBLICATIONS

Wellesley company sends body montiors into space Crum Apr. 1998.
Wireless transmission of a color television moving image from the stomach using a miniature CCD camera light source and microwave transmitter Swain CP Gong F Mills TN Gastrointest Endosc 1997;45:AB40.
BBC News Online—Pill camera to 'broadcast from the gut' Feb. 21, 2000 www.news bbc co uk.
Biomedical Telemetry R Stewart McKay, John Wiley and Sons 1970 p. 244-245.

* cited by examiner

SYSTEM AND METHOD FOR CHANGING TRANSMISSION FROM AN IN VIVO SENSING DEVICE

PRIOR APPLICATION DATA

The present application is a continuation of U.S. patent application Ser. No. 10/200,548 entitled "SYSTEM AND METHOD FOR CHANGING TRANSMISSION FROM AN IN VIVO SENSING DEVICE" filed Jul. 23, 2002 now U.S. Pat. No. 6,934,573 which in turn claims benefit from prior U.S. provisional application No. 60/306,872 entitled "VARIABLE SIGNAL STRENGTH IMAGING DEVICE" filed on Jul. 23, 2001, all of which being incorporated by reference herein in their entirety.

FIELD OF THE INVENTION

The present invention relates to an in vivo sensing device, system and method such as for imaging the digestive tract; more specifically, to an in vivo sensing device utilizing a device, system and method whereby the transmission signal strength may be varied.

BACKGROUND OF THE INVENTION

Devices and methods for sensing of passages or cavities within a body, and for gathering information (e.g., image data, pH data, temperature information, pressure information), are known in the art. Such devices may include, inter alia, various endoscopic imaging systems and devices for performing imaging in various internal body cavities. Some devices transmit the collected data to an external receiving unit.

An in-vivo imaging device may include, for example, an imaging system for obtaining images from inside a body cavity or lumen, such as the gastrointestinal (GI) tract. The imaging system may include, for example, an illumination unit, such as a set of light emitting diodes (LEDs), or other suitable light sources. The device may include an imaging sensor and an optical system, which focuses the images onto the imaging sensor. A transmitter and antenna may be included for transmitting the images signals. A receiver/recorder, for example worn by the patient, may record transmitted image data and store image and other data. The recorded data may then be downloaded from the receiver/recorder to a computer or workstation for display and analysis.

A signal transmitted from an in vivo sensor may be attenuated while passing through the body tissues, due to the fact that tissues have electrical conductance. Continuous high-level transmission, which might overcome the attenuation, may require a continuous supply of high energy, may be inefficient and may be in conflict with regulatory considerations.

Therefore, there is a need for an in-vivo sensing device, such as an imaging device, which may transmit data at efficient power levels.

SUMMARY OF THE INVENTION

An embodiment of the device, system and method of the present invention enables obtaining in vivo images from within body lumens or cavities, such as images of the gastrointestinal (GI) tract. One embodiment of the invention provides a device including an imaging system and a radio frequency (RF) transmitter for transmitting signals from an imaging device to a receiving system. In one embodiment of such an imaging system, the signal strength of the transmitter may be varied or changed to account for, for example, the amount of signal attenuation resulting from body tissues.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

The device, system and method of the present invention may be used with an imaging system or device such as that described in WO 01/65995 entitled "A Device And System For In Vivo Imaging", published on 13 Sep. 2001, which is hereby incorporated by reference. However, the device, system and method according to the present invention may be used with any device providing data from a body lumen or cavity. For example, the device, system and method of the present invention may be used with imaging devices using cameras other than CMOS imaging cameras. In alternate embodiments, a known imaging camera of another type such as a CCD may be used. A further example of an imaging system and device with which the system and method of the present invention may be used is described in U.S. Pat. No. 5,604,531 entitled "In Vivo Video Camera System," which is incorporated herein by reference. In further embodiments, the system and method of the present invention may be used with devices and systems capturing information other than image information within the human body; for example, pressure or pH information, information on the location of a transmitting device, or other information.

Figure 1:
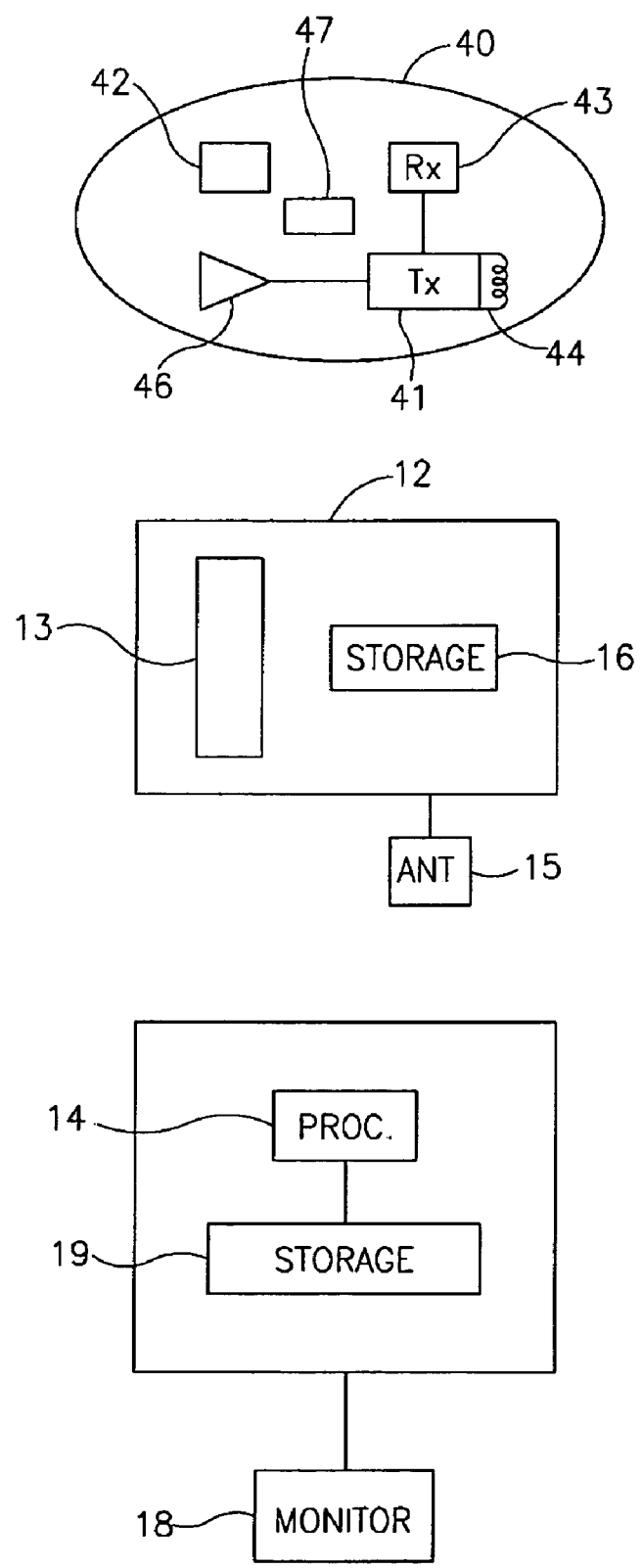
FIG. 1 shows a schematic diagram of an in vivo imaging system according to one embodiment of the present invention.

Reference is made to FIG. 1, which shows a schematic diagram of an in vivo sensor according to one embodiment of the present invention. In an exemplary embodiment, the system includes a device 40 having an image sensor 46, for capturing images, an optical system (not shown), an illumination source 42 (which may be, for example, one or more LEDs, although any suitable illumination source), for illuminating the body lumen, and a transmitter 41 and antenna 44, for transmitting image and possibly other information to a receiving device. Typically, the device 40 is an ingestible capsule capturing images, but may be another sort of device and may collect information other than image information. An optical system (not shown), including, for example, lenses or mirrors, may aid in focusing reflected light onto the imager 46. The device 40 typically includes a power source 47 which may be, for example, one or more a batteries or other power sources.

The device 40 may be swallowed or otherwise ingested by a patient and typically traverses the patient's GI tract. In one embodiment, transmitter 41 provides control and possibly other processing capability for the device 40. Thus, transmitter 41 may include or be associated with circuitry such as an ASIC, a microcontroller, or a "computer on a chip." In alternate embodiments, a separate control and/or processing unit may be provided.

In one embodiment, the imager 46 is a complementary metal oxide semiconductor (CMOS) imaging camera. The CMOS imager is typically an ultra low power imager, has a low sensitivity to the red spectrum, and is provided in chip scale packaging (CSP). One suitable CMOS camera is, for example, a "camera on a chip" CMOS imager specified by Given Imaging Ltd. of Israel and designed by Photobit Corp. of California, USA, with integrated active pixel and post processing circuitry. Other types of CMOS imagers may be used. In another embodiment, another imager may be used, such as a CCD imager, or another imager.

In one embodiment, transmitter 41 includes at least a modulator for receiving an image signal from the imager 46, a radio frequency (RF) amplifier, an impedance matcher and an antenna. The modulator converts the input image signal having a cutoff frequency $f_c$ of less than 5 MHz to an RF signal having a carrier frequency $f_r$, typically in the range of 1 GHz. While in one embodiment, the signal is an analog signal, the modulating signal may be digital rather than analog. The carrier frequency may be in other bands, e.g. a 400 MHz band. The modulated RF signal has a bandwidth of $f_r$. The impedance matcher matches the impedance of the circuit to that of the antenna. Other transmitters or arrangements of transmitter components may be used. For example, alternate embodiments may not include a matched antenna or may include a transmitter without a matching circuit. In alternate embodiments, the device 40 may have different configurations and include other sets of components. Other frequencies may be used. In yet further embodiments, sensors other than image sensors may be used, such as pH meters, temperature sensors, pressure sensors, etc. and input RF signals other than image signals may be used.

According to one embodiment, while the device 40 traverses a patient's GI tract, the device 40 transmits image and possibly other data to components located outside the patient's body, which receive and process the data. Typically, located outside the patient's body in one or more locations, are an image receiver 12, typically including an antenna 15 or antenna array, an image receiver storage unit 16, a data processor 14, a data processor storage unit 19, and an image monitor 18, for displaying, inter alia, the images transmitted by the device 40 and recorded by the image receiver 12. According to one embodiment, the image receiver 12 and image receiver storage unit 16 are small and portable, and are worn on the patient's body during recording of the images. Typically, data processor 14, data processor storage unit 19 and monitor 18 are part of a personal computer or workstation, which includes standard components such as processor 14, a memory, a disk drive, and input-output devices, although alternate configurations are possible.

In alternate embodiments, the data reception and storage components may be of another configuration. Further, image and other data may be received in other manners, by other sets of components. Typically, in operation, image data is transferred to the data processor 14, which, in conjunction with, for example, a central processing unit and software, stores, possibly processes, and displays the image data on monitor 18. Other systems and methods of storing and/or displaying collected image data may be used.

Typically, the device 40 transmits image information in discrete portions. Each portion typically corresponds to an image or frame. Other transmission methods are possible. For example, the device 40 may capture an image once every half second, and, after capturing such an image, transmit the image. Other capture rates are possible Typically, the image data recorded and transmitted is digital color image data, although in alternate embodiments other image formats (e.g., black and white image data) may be used. In one embodiment, each frame of image data includes 256 rows of 256 pixels each, each pixel including data for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by, for example, a one byte (i.e., 0-255) brightness value. Other data formats may be used.

The receiver 12 typically detects a signal having the carrier frequency $f_r$ and the bandwidth $f_c$ described hereinabove. The receiver 12 may be similar to those found in televisions or it may be one similar to those described on pages 244-245 of the book Biomedical Telemetry by R. Stewart McKay and published by John Wiley and Sons, 1970. The receiver may be digital or analog. In alternate embodiments, other receivers may be used.

The location of the imaging device 40 inside the body and its orientation relative to the antenna(s) 15 change as the device 40 traverses the GI tract. At times the device 40 may be located close to the body surface, and at other times it may be located deeper inside the body. The signal transmitted from the device 40 may be attenuated while passing through the body tissues, due to the fact that tissues have electrical conductance. The level of attenuation may be affected by, inter alia, the amount and types of body tissue that the signal passes through, and on the transmission frequency. Attenuation typically increases logarithmically with the frequency. In one embodiment of such an imaging device 40, transmission occurs at a frequency of 434 MHz, using Phase Shift Keying (PSK); the body tissue attenuation at this frequency is approximately 2.5-3 dB/cm. In alternate embodiments, other transmission frequencies and other methods (such as AM or FM) may be used.

One method for maintaining a reliable communication channel for practically all possible (or likely) locations of the device 40 inside the body is to set the transmission power of the transmitter 41 in the device 40 to some maximum amount such that proper transmission between the device 40 and the antenna 15 or antenna array is achieved for all locations. For example, assuming that the maximal depth in the body, of which the device 40 is to traverse (e.g., the GI tract) is 25 cm, the transmitter 41 transmission output should be higher than the minimum power level required by the receiver 12 by, for example, 3 dB/cm*25 cm=75 dB; the total power level required is the minimum required level of the receiver 12 plus 75 dB. The minimum required level is a typically empirical value which depends, inter alia, on the sensitivity of the receiver 12, on the modulation technique being used as well as on the specific design of the receiver 12. In such an "open loop" embodiment, high-level transmission levels occur continually, even when lower power transmission may be satisfactory. High power transmission requires the transmitter 41 to consume high levels of power; if the system operates on batteries, the batteries are emptied faster. Further, government regulatory considerations may limit transmission levels.

In one embodiment of the device, system and method of the present invention, a "closed loop" is used, with feedback from the receiver 12 or another module altering the power transmission level of the transmitter 41 in the device 40 in order to ensure that the power level is high enough, but not higher than necessary, or not significantly higher than necessary, to allow for acceptable transmission quality. Typically, the receiver 12 measures the power level of the received signal from the imaging or other device 40. Various known methods of measuring the strength of the received signal may be used. In one embodiment, at the start of the transmission of an image frame or other unit of transmission, a blank or dummy section is sent. During the transmission of this section, the receiver 12 samples signals from each of typically multiple antennas in the antenna array 15, and determines which antenna is receiving and is the source of the strongest signal. This antenna is used to receive the image frame, and the strength of this signal determines the signal strength. In alternate embodiments, only one antenna may be used, and this antenna is then used to determine signal strength. Embodiments of the present invention may be used with devices or systems not transmitting "frames" of data, and may be used with systems transmitting data continuously.

In one embodiment, to regulate the signal strength of the transmitter 41, if the receiver 12 determines that the signal strength is below a lower threshold which will result in clear transmission, it determines that the signal strength of the transmitter 41 should be increased, and if the image receiver 12 determines that the signal strength is above an upper threshold, it determines that the signal strength of the transmitter 41 should be decreased. In alternate embodiments, other methods of controlling the signal strength may be used. For example, after each frame is received, the received signal strength may be evaluated and the signal strength of the transmitter 41 may be adjusted. A blank frame need not be used.

A power level transmitter 13 within the receiver 12, typically a simple transmitter (e.g., a transmitter transmitting a relatively small amount of information using simple modulation or Frequency Shift Keying (FSK), using a relatively low frequency signal), transmits a signal to the device 40 regarding the power level of the received signal. In the imaging or other device 40 a typically simple power level receiver 43 (e.g., a simple RF receiver, such as a receiver in the alarm of a car) may be used to receive and decode power level information, and the output power of the transmitter within the device 40 is changed accordingly.

Typically, the power level transmitter 13 may transmit a command from a predetermined set of commands. The receiver 43 may receive and decode the command, and transfer it to the transmitter 41, in order to set the output power level. In alternate embodiments, other power level information may be used; for example, a signal to raise or lower the power level by a certain amount, or a signal indicating the power level or signal quality. In further embodiments, processing capability may be included in the device 40 for adjusting the power level based on such signals. According to one embodiment a processing unit may be included in the device 40 for processing the power level data received from the power level transmitter 13 and for commanding the transmitter 41 to adjust the transmission level. In one embodiment, transmitter 41 may provide processing unit capabilities, thus transmitter 41 may adjust its own power levels. According to alternate embodiments a processing unit may be included in the receiver 12 for processing the signal received from transmitter 41 and for regulating the signal transmitted from power level transmitter 13. The transmitter 41 may include circuitry, which may enable it to change the level of the output signal, i.e. the level of the signal that is transmitted through the antenna. The level of the transmitted signal may be determined by different methods, e.g. it may be set constant, or may be changed after receiving a command by the power level receiver 43.

In alternate embodiments, the power level transmitter 13 and power level receiver 43 need not be simple devices. In further embodiments, a device other than the receiver 12, which may include a power level receiver, may provide feedback to the device 40.

In yet further embodiments the power level transmitter 13 may be used to transmit a constant, typically, periodical and known signal to be received by the power level receiver 43. The signal is typically attenuated (e.g., by the passage through the body tissues) such that the received signal contains information regarding the attenuation. As such, the received signal may provide indication of the transmission strength required from transmitter 41. According to embodiments of the invention the device 40 may include a processor, typically, for computing the transmission strength of a transmitted signal based on a received signal, for example, a signal received from the power level transmitter 13.

According to one embodiment two image frames are transmitted from the device 40 every second, and with the transmission of each frame, the signal strength is measured by the receiver 12 and a power level feedback signal is provided to the device 40. In alternate embodiments, other rates of imaging and other rates of feedback may be used. For example, feedback may be provided once every several frames or periodically, per a fixed time period.

Figure 2:
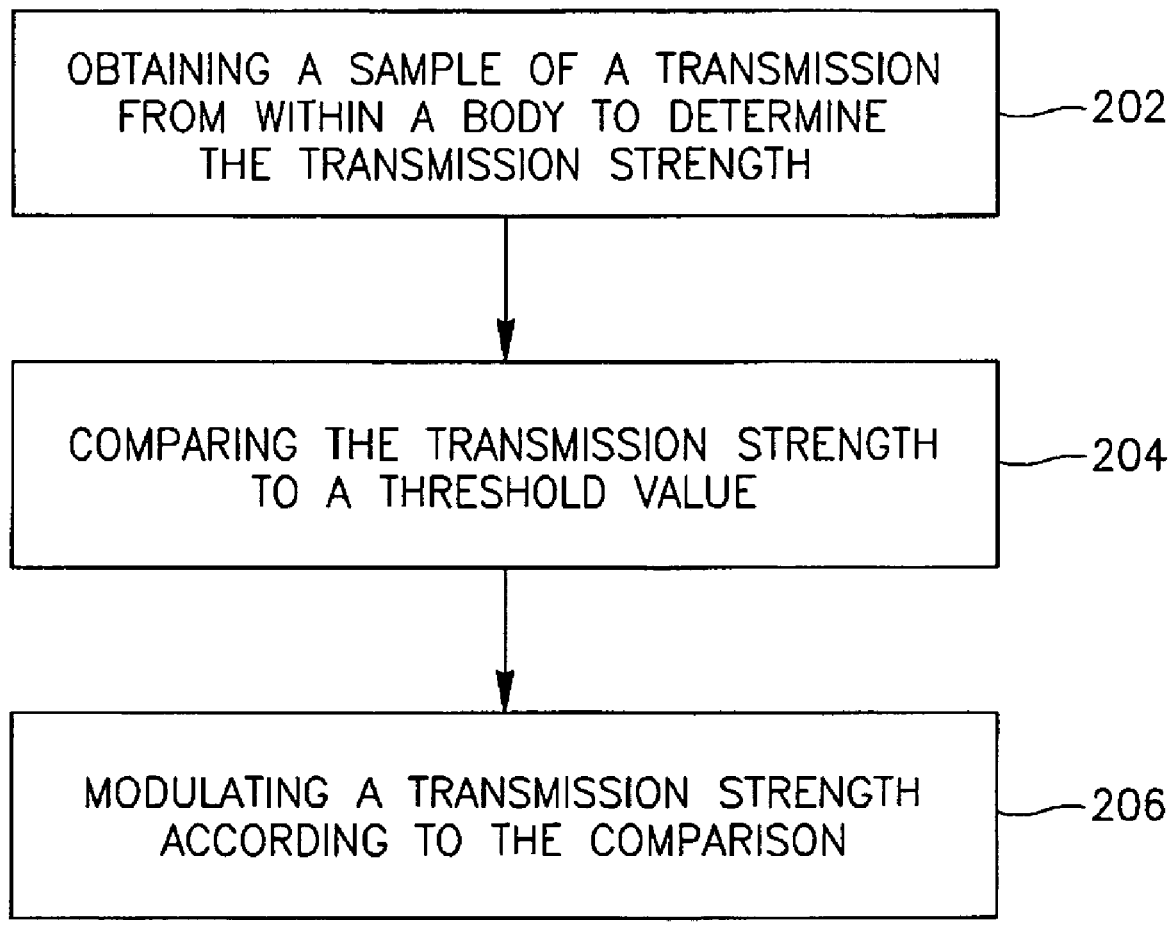
FIG. 2 shows a block diagram of a method for changing data transmitted from an in vivo sensing device, according to an embodiment of the invention.

Reference is now made to FIG. 2, which shows a block diagram of a method for changing data transmission from an in vivo sensing device. According to one embodiment the method includes the steps of obtaining a transmission from within a body and in response to the transmission, changing transmission strength. According to an embodiment of the invention, the method includes the steps of obtaining a sample of a transmission from within a body (202) to determine the transmission strength; comparing the transmission strength to a threshold value (204); and changing (for example, decreasing or increasing) a transmission strength according to the comparison (206). According to one embodiment one transmission event is sampled, for example, by measuring the transmission strength of a blank or dummy portion of the transmission, and the same transmission event is changed. According to another embodiment one transmission event is sampled and another transmission event is changed, for example, transmission n is sampled and the transmission strength of n is determined and compared to a threshold. Transmission n+1 is then changed according to the comparison. Other sampling methods or frequencies may be used.

According to an embodiment of the invention a method for controlling image data transmission from an in vivo capsule is provided. The method according to an embodiment may include receiving a transmission having a signal strength; evaluating the signal strength; and altering a capsule transmission power level.

Accordingly, lower average power consumption in the device 40 may be achieved, prolonging battery life (if a battery is used). Furthermore, in situations where the estimated maximum power level is not enough to achieve reliable communication, the power level can be increased by the closed loop system, allowing for more reliable communication.

It will be appreciated by persons skilled in the art that the present invention is not limited to what has been particularly shown and described hereinabove. Alternate embodiments are contemplated which fall within the scope of the invention.

The invention claimed is:

1. A swallowable capsule for in vivo sensing comprising:
a sensor to obtain in-vivo data;
a transmitter to transmit said in-vivo data;
a RF receiver; and a controller for controlling a transmission power level of data transmitted by said transmitter, wherein said controller controls said transmission power level of data transmitted by said transmitter based on a signal received from said RF receiver.

2. The device according to claim 1 wherein the swallowable capsule comprises an image sensor, wherein the transmitter transmits image data obtained by said image sensor, and wherein said controller in said capsule controls said transmission power level of said image data transmitted by said transmitter based on said power level signal received at said RF receiver.

3. The device according to claim 1 wherein the transmitter transmits image data, and wherein said power level signal is based on the power level of said transmitted image data.

4. The device according to claim 1 wherein the transmitter transmits using PSK.

5. The device according to claim 1 wherein the RF receiver is capable of receiving a power level signal from an external power level transmitter.

6. The device according to claim 1 wherein the RF receiver is to receive a command from a predetermined set of commands.

7. The device according to claim 1 comprising a processor for determining a power level of transmission of data transmitted by said transmitter and communicating said power level to said controller.

8. The device according to claim 7 wherein the processor is to process power level data received at said RF receiver from an external power level transmitter.

9. The device according to claim 1, wherein said sensor comprises an imager, and wherein said in-vivo data is in-vivo linage data.

10. The device according to claim 1, wherein said controller increases said transmission power level of data transmitted by said transmitter if said signal received from said RF receiver is below a lower threshold and wherein said controller decreases said transmission power level of data transmitted by said transmitter if said signal received from said RF receiver is above an upper threshold.

11. A system for in vivo sensing inside the body of a patient comprising:
a swallowable capsule for in vivo sensing comprising a sensor to obtain in-vivo data, a transmitter to transmit said in-vivo data, a RF receiver, and a controller for controlling a transmission power level of data transmitted by said transmitter; and
a receiver located outside of the patient's body to receive a signal transmitted by the transmitter of said capsule, said signal representing said in-vivo data, and transmit a power level signal based on a power level of said signal, wherein said controller in said capsule controls said transmission power level of data transmitted by said transmitter based on said power level signal received at said RF receiver.

12. The system according to claim 11 wherein the sensor of the swallowable capsule comprises an image sensor, wherein said transmitter is to transmit image data acquired by said image sensor, and wherein said controller in said swallowable capsule controls said transmission power level of said image data transmitted by said transmitter based on said power level signal received at said RF receiver.

13. The system according to claim 11 wherein the in vivo data transmitted by the transmitter of said swallowable capsule is image data, and wherein said power level signal is based on the power level of said transmitted image data.

14. The system according to claim 11 wherein the transmitter of said swallowable capsule transmits using PSK.

15. The system according to claim 11 wherein the RF receiver is to receive a command from a predetermined set of commands.

16. The system according to claim 11, wherein said controller of said swallowable capsule increases said transmission power level of data transmitted by said transmitter if said signal received from said RF receiver is below a lower threshold and wherein said controller decreases said transmission power level of data transmitted by said transmitter if said signal received from said RF receiver is above an upper threshold.

17. The system according to claim 11 wherein said capsule further comprises a processor for determining a power level of transmission of data transmitted by said transmitter and communicating said power level to said controller.

18. The system device according to claim 17 wherein the processor of said capsule is to process power level data received at said RF receiver from an external power level transmitter.

* * * * *